United States Patent [19]

Gors et al.

[11] Patent Number: 5,068,447

[45] Date of Patent: Nov. 26, 1991

[54] FRIEDEL-CRAFTS PREPARATION OF AROMATIC KETONES WITH AN INOGANIC SALT CONTROLLING AGENT

[75] Inventors: Heinrich C. Gors, Mountain View; Patrick J. Horner, Menlo Park; Viktors Jansons, Los Gatos, all of Calif.

[73] Assignee: Raychem Corporation, Menlo Park, Calif.

[21] Appl. No.: 550,246

[22] Filed: Jul. 6, 1990

Related U.S. Application Data

[60] Continuation of Ser. No. 293,726, Jan. 5, 1989, abandoned, which is a division of Ser. No. 175,646, Mar. 21, 1988, Pat. No. 4,814,508, which is a continuation of Ser. No. 874,268, Jun. 13, 1986, abandoned, which is a continuation-in-part of Ser. No. 789,546, Oct. 22, 1985, abandoned, which is a continuation-in-part of Ser. No. 659,598, Oct. 11, 1984, abandoned.

[51] Int. Cl.$^5$ .................. C07C 107/06; C07C 49/813
[52] U.S. Cl. ..................................... 568/309; 568/315; 568/322; 568/323; 568/325; 568/333; 534/588; 534/598; 549/43; 549/433; 549/234
[58] Field of Search ................. 534/588, 598; 568/309, 568/315, 322, 323, 325, 333

[56] References Cited

U.S. PATENT DOCUMENTS

| | | | |
|---|---|---|---|
| 1,874,582 | 2/1932 | Nawiasky | 568/333 X |
| 2,773,903 | 7/1956 | Hardy et al. | 568/333 X |
| 2,853,522 | 5/1958 | Dayan et al. | 568/333 |
| 2,853,523 | 4/1958 | von Glahn et al. | 568/333 |
| 2,861,104 | 7/1958 | von Glahn et al. | 568/333 |
| 2,861,105 | 3/1958 | Stanley et al. | 568/333 |
| 3,282,989 | 1/1966 | Renckoff et al. | 568/333 |
| 4,814,508 | 3/1989 | Gors et al. | 534/586 |

FOREIGN PATENT DOCUMENTS

| | | | |
|---|---|---|---|
| 0069598 | of 0000 | European Pat. Off. | 568/332 |
| 0024286 | 3/1981 | European Pat. Off. | 568/332 |
| 0878647 | of 0000 | Fed. Rep. of Germany | 568/332 |
| 0913891 | of 0000 | Fed. Rep. of Germany | 568/332 |
| 2014514 | of 0000 | Fed. Rep. of Germany | 568/332 |
| 384807 | of 0000 | U.S.S.R. | 568/332 |
| 384813 | of 0000 | U.S.S.R. | 568/332 |
| 1088339 | of 0000 | United Kingdom | 540/122 |
| 1420506 | of 0000 | United Kingdom | 568/332 |
| 2103604 | of 0000 | United Kingdom | 568/332 |

OTHER PUBLICATIONS

Freitag, Chem. Abs. 95:43910a.
Windholz, Chem. Abs. 73:120343t.
Braun Chem. Abs. 50:4229i.
Braun, Chem. Abs. 52:14691f.
Moshehinskaya, Chem. Abs. 79:104903u.
Olah, "Friedel-Crafts and Related Reactions," vol. I, Interscience Publishers, Inc. N.Y., pp. 91–109, 120, 122–123, and 212–304 (1963).

*Primary Examiner*—Mary C. Lee
*Assistant Examiner*—Peter Davis
*Attorney, Agent, or Firm*—Yuan Chao; Herbert G. Burkard

[57] ABSTRACT

Aromatic carbonyl compounds, in particular arylene ether ketones, are prepared by reacting an appropriate reagent system in the presence of free Lewis acid and a complex between a Lewis acid, for example, aluminum trichloride, and an inorganic salt controlling agent, for example, lithium chloride, and, optionally, a diluent, such as methylene chloride. The process is particularly advantageous for the preparation of substantially or all para-linked arylene ether ketones as the presence of the Lewis acid/Lewis base complex markedly reduces alkylation and ensures the substantial absence of ortho substitution.

7 Claims, No Drawings

FRIEDEL-CRAFTS PREPARATION OF AROMATIC KETONES WITH AN INOGANIC SALT CONTROLLING AGENT

This application is continuation of application Ser. No. 07/293,726, filed Jan. 5, 1989, now abandoned which is a division of application Ser. No. 07/175,646, filed Mar. 21, 1988, now U.S. Pat. No. 4,814,508, which is a continuation of application Ser. No. 06/874,268 filed June 13, 1986, now abandoned, which is a continuation-in-part of application Ser. No. 06/789,546, filed Oct. 22, 1985, now abandoned, which is a continuation-in-part of application Ser. No. 06/659,598, filed Oct., 11, 1984, now abandoned, the disclosures of which are incorporated herein by reference.

BACKGROUND OF THE INVENTION

This invention relates to the preparation of aryl carbonyl compounds, and in particular to para substituted aryl carbonyl compounds.

Aryl carbonyl compounds are useful in the preparation of poly(arylene ether ketones). In the preparation of these polymers it is essential that the monomers used be in a highly pure state to prevent undesirable side reactions. Furthermore, the polymers obtained should be stable enough to survive extrusion without undue deleterious effects on their physical properties. The substitution pattern of the monomers used can control the properties of the polymers synthesized, and it is generally recognized that the highest melting points and glass-rubber transition temperatures are obtained with all para linked polymers. Mixtures of substitution isomers are used when polymers of reduced crystallinity or lowered $T_g$ are required, but the all para substituted polymers are most preferred. When mixtures of monomers are used, known ratios of the different isomers are needed, necessitating the use of pure starting materials. The present invention relates to a process for the preparation of aryl carbonyl compounds that improves outstandingly the degree of purity of the product and/or the degree of para substitution.

Aryl carbonyl compounds are also useful as chemicals and chemical intermediates, for example, in the pharmaceutical and agricultural chemicals, dyestuffs and general chemical additives area. Here too it is frequently found that the all para substituted carbonyl compounds are the most useful. Avoidance of concurrent formation of other isomeric byproducts in the synthesis of such compounds is always beneficial economically and in some instances is essential because some isomeric compounds which are difficult to remove have been found to be toxic or even carcinogenic.

SUMMARY OF THE INVENTION

In accordance with the process Of this invention, the Friedel-Crafts condensation of appropriate reactants is controlled to suppress side reactions including alkylation and/or ortho substitution by the addition of an inorganic salt controlling agent to the reaction medium.

One aspect of this invention comprises a method of producing an aryl carbonyl compound which comprises reacting phosgene or an organic carboxylic acid, acid halide, alkyl ester or anhydride together with an aromatic comonomer containing at least one activated hydrogen atom in the presence of a Lewis acid, an inorganic salt controlling agent, and a nonprotic diluent, the various components being present in such proportions and the reaction being conducted under such conditions that a para substituted carbonyl compound substantially free of by-products resulting from alkylation and/or ortho substitution is obtained.

Another aspect of this invention provides a process for the preparation of an aromatic carbonyl compound having the formula

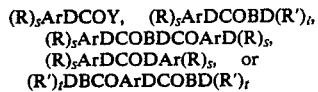

wherein each s and t is independently 1, 2 or 3 and each R, Ar, B, D and R' is independently as defined below, which process comprises reacting a first reactant, consisting of a substituted or unsubstituted aromatic compound containing at least one activated hydrogen atom of the formula

wherein Ar is a homo or hetero-aromatic mono-, di- or tri-cyclic moiety or a fused homo-aromatic condensed system containing less than 20 aromatic carbon atoms, or a heteroaromatic system containing less than 8 nitrogen atoms, each R is defined below and D is

wherein n, m, and p are each independently 0, 1, 2 or 3, provided that n+m+p is less than 4, and Z is —CO—, —SO$_2$—,

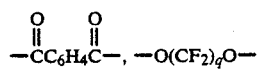

or V, provided that when n+m+p>0, any Ar group which contains an activated hydrogen atom is also linked to a V group, where V is a divalent radical of the formula

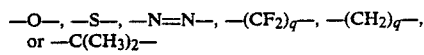

wherein q is 1 to 20; with a second reactant, consisting of phosgene, or a monofunctional acyl compound of the general formula

or a di-functional acyl Compound of the general formula

wherein each B is independently a divalent substituted or unsubstituted aliphatic or cycloaliphatic group or Ar, and R and R' which may be the same or different are a H, Br, Cl or F atom or a hydroxy, alkoxy, alkyl, aralkyl, unsubstituted or mono- or disubstituted amino, nitro, ester, acid, amide or imide group, and each Y represents a Br, Cl or F atom or a hydroxy or alkoxy group, subject to the proviso that any aromatic ring which contains an activated hydrogen atom also contains less than 2 alkoxy groups and to the further proviso that the aromatic carbonyl compound contains less than 2 identical directly linked sequences containing at least one —SO$_2$— or —CO— in a reaction medium comprising:
  A) an inorganic salt controlling agent in an amount from 0 to 4 equivalents per equivalent of acid, ester or acid halide group in the reactants;
  B) a Lewis acid in an amount of about one equivalent per equivalent of carbonyl, or other basic species in the reactants plus one equivalent per equivalent of Lewis base plus an amount effective to act as a catalyst for the reaction; and
  C) a non-protic diluent in an amount from about 20 to about 93% by weight, based on the weight of the total reaction mixture.

Pendant substituents which can be present on B or Ar groups include, for example, lower alkyl, cyano, halogen, nitro, benzoyl or any other atom or group which will not interfere with the reaction by virtue of either its chemical nature of its location in the reactant from which the B group is derived.

DETAILED DESCRIPTION OF THE INVENTION

The term "activated hydrogen atom" refers to a hydrogen atom displaceable under the electrophilic (Friedel-Crafts) reaction conditions employed in the reaction.

Aromatic compounds suitable for acylation according to the process of the instant invention exhibit carbon-13 nuclear magnetic resonance (C-13 NMR) chemical shifts at the ring site where acylation is desired at least 2.1, preferably at least 2.4 and most preferably at least 2.8 parts per million (ppm) less than that exhibited by benzene. For a listing of C-13 NMR chemical shifts of monosubstituted benzenes see M. Mishima et al (Memoirs of the Faculty of Science, Kyushu Un., Ser. C, Vol. 11 no. 1, 1978) hereby incorporated by reference. Table 2 of this reference lists C-13 NMR chemical shifts of a variety of monosubstituted benzenes measured in solution in carbon tetrachloride. Benzene in this solvent is stated to have a chemical shift of 128.04 ppm. The aromatic compounds useful in the instant invention may, but preferably do not, form additional complexes with Lewis acid under the reaction conditions. Those skilled in the art will readily recognize that when an addition complex is formed, it should not substantially deactivate the molecule to acylation. Thus such complexes, for example, should still exhibit C-13 NMR chemical shifts which are at least 2.1 ppm less than that of benzene or should contain sufficient uncomplexed aromatic compound is present to enable the reaction to proceed at the desired rate.

Illustrative aromatic compounds of the general formula (R)$_x$ArDH are: benzene, toluene, ethyl benzene, fluorobenzene, anisole, ethoxy benzene, 3-chloroanisole, naphthalene, anthracene and

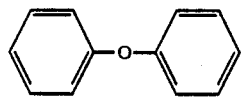

-continued

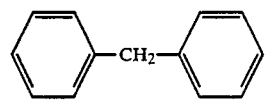

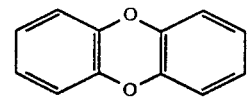

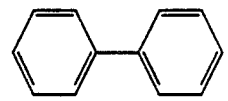

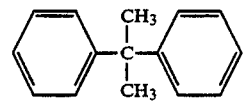

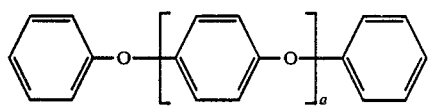

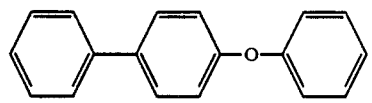

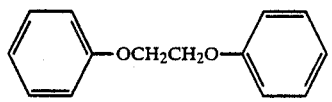

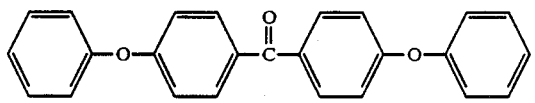

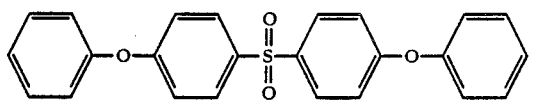

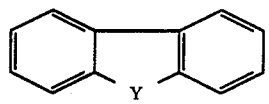

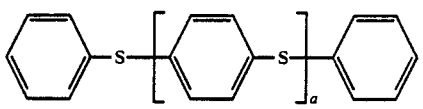

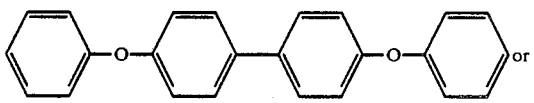 or

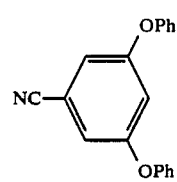

wherein each a is independently 0, 1 or 2 and V is as defined above.

Illustrative mono or di-acyl compounds of the general formula

YCOBD(R)$_t$, O(COBD(R')$_t$)$_2$ or YCOBDCOY are: acetic anhydride, acetyl chloride, adipoyl dichloride, benzoyl chloride, 4-fluorobenzoyl chloride, 4-chlorobenzoyl chloride, 3-nitrobenzoyl chloride, phthaloyl chloride, phthalic anhydride, naphthoyl chloride, benzenesulfonyl chloride, p-toluenesulfonyl chloride, tetrabromophthaloyl chloride, and compounds of the following formulas

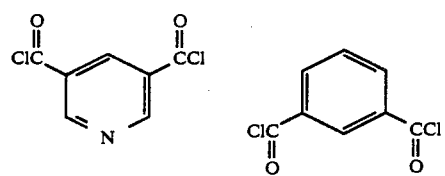
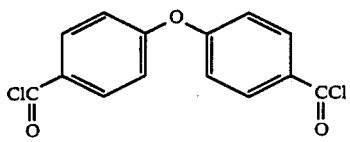
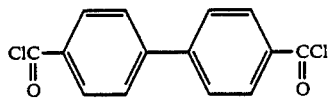
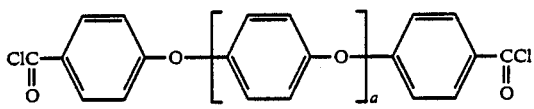
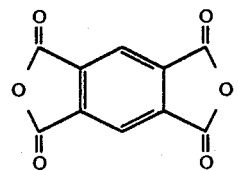
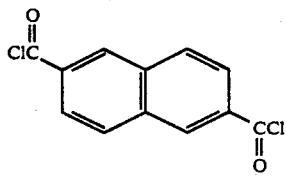
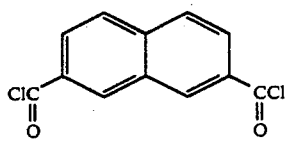

-continued

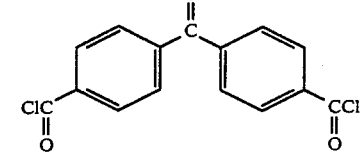
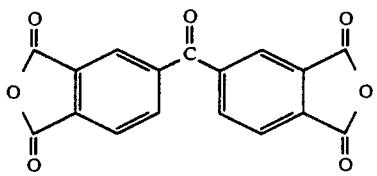
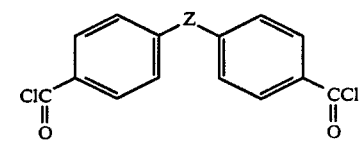
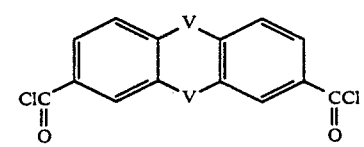
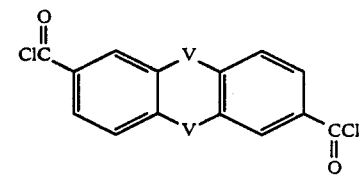

wherein each V is independently as defined above and Z and a are as defined above.

Preferred acylating agents are phosgene, sulfuryl chloride and acyl compounds such as 4-fluorobenzoic acid or acid halide, iso- or tere-phthalic acid or acid halide, naphthalene 2,6-dicarboxylic acid or acid halide, diphenyl ether 4,4'-dicarboxylic acid or acid chloride and benzopheneone 4,4'-dicarboxylic acid or acid chloride.

Preferred combinations of substituted aromatic compounds and acyl compounds are fluorobenzene or diphenyl ether with 4-fluorobenzoyl chloride, ethyl 4-fluorobenzoate, acetyl chloride, acetic anhydride, iso- or tere-phthaloyl chloride, 4-hydroxybenzoyl chloride and 4-(4-hydroxyphenoxy)-benzoyl chloride.

In carrying out the process of this invention, equivalent amounts of the substituted aromatic compound and the aromatic acyl compound are preferably employed, although it may be advantageous in certain circumstances to use up to about a molar excess of one reactant.

The reagent system is reacted in the presence of a reaction medium comprising:

A) an inorganic salt controlling agent in an amount from 0 to 4 equivalents per equivalent of acid, ester or acid halide group in the reactants;

B) a Lewis acid in an amount of about one equivalent per equivalent of carbonyl or other basic species in the reactants plus one equivalent per equivalent of Lewis base plus an amount effective to act as a catalyst for the reaction; and C) a non-protic diluent in an amount from about 20 to about 93% by weight, based on the weight of the total reaction mixture.

The term "Lewis acid" is used herein to refer to a substance which can accept an unshared electron pair from another molecule. Lewis acids which can be used in the practice of this invention include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. The use of substantially anhydrous aluminum trichloride as the Lewis acid is preferred.

The amount of Lewis acid used in the practice of this invention varies depending on the particular starting materials and reaction medium selected. In all instances where the Lewis acid forms a complex with carbonyl groups or other organic species in the reactants forming a complex with Lewis acid (hereinafter called "other basic species") irreversibly under the reaction conditions, at least about one equivalent of Lewis acid per equivalent of carbonyl groups or other basic species present in the starting materials is used plus an amount effective to act as a catalyst for the acylation. Generally the catalytic amount added is from about 0.05 to about 0.3 equivalents of Lewis acid per equivalent of acid, ester or acid halide in the reaction mixture. As is well known to those skilled in the art, acids, esters and many acid anhydrides react with an excess of Lewis acids such as aluminum trichloride to yield the corresponding acid halide which then serves as the actual acylating agent. As indicated above, the Friedel-Crafts acylation reaction is controlled by the addition of an ionic controlling agent.

In a preferred embodiment of the invention, the ionic controlling agent suppresses undesirable side reactions, whether by acylation or by alkylation.

Preferred inorganic salt controlling agents for the acylation reaction are Lewis bases. The term "Lewis base" is used herein to refer to a substance capable of donating an unshared electron pair to a Lewis acid. Thus, the Lewis base forms a complex with the Lewis acid used in the reaction medium. It has been found that Lewis bases which form a 1:1 complex having a heat of association at least about that of diphenylether with the Lewis acid are preferred. For example, where aluminum trichloride is the Lewis acid the Lewis base used should form a 1:1 complex having a heat of association of at least about 15 kcal/mole, preferably at least about 30 kcal/mole. While the heats of association are for a 1:1 Lewis acid/Lewis base complex consisting solely of these two components, the actual complex formed in the reaction medium need not be a 1:1 complex. A discussion on heats of association for Lewis acid/Lewis base complexes is found in J. Chem. 50C. (A), 1971, pages 3132–3135 (D.E.H. Jones et al). The Lewis base used should not be an acylating, alkylating or arylating agent nor should it be acylatable under the reaction conditions.

Mixtures of two or more Lewis bases can be used if desired. The Lewis base used as an inorganic salt controlling agent in the practice of this invention is an additional component added to the reaction medium. This does not include basic species formed in situ during the acylation. When a Lewis base is used as an inorganic salt controlling agent, an additional amount of Lewis acid generally about one equivalent per equivalent of Lewis base is used. When aluminum chloride is used as the Lewis acid one equivalent is considered to be $AlCl_3$.

Suitable inorganic salt controlling agents include inorganic salts which can form complexes with Lewis acids, for example, chlorides, such as trimethylammonium chloride, tetramethylammonium chloride, sodium chloride or lithium chloride, perchlorates, trifluoromethanesulfonates and the like.

Preferred inorganic salt controlling agents for the practice of this invention are trimethylamine hydrochloride, tetramethylammonium chloride, 1-ethylpyridinium chloride, lithium chloride, lithium bromide, sodium chloride, sodium bromide, potassium chloride, potassium bromide and mixtures thereof.

The amount of inorganic salt controlling agent present should be from 0 to about 4 equivalents per equivalent of acid halide groups present in the reagent system. Amounts greater than 4 equivalents could be employed, if desired. However, no additional controlling effect is usually achieved by adding larger amounts. Thus, it is preferred to use no more than about 4 equivalents and generally about 2 equivalents. When an inorganic salt controlling agent is added to control the reaction at least about 0.1, preferably at least about 0.2 and most preferably at least about 0.5 equivalents of inorganic salt controlling agent per equivalent of acid halide groups present should be used. The particular amount of inorganic salt controlling agent added depends to a certain extent on the nature of the monomers present.

The temperature at which the reaction is conducted can be from about $-50°$ C. to about $+150°$ C. It is preferred to start the reaction at lower temperatures, for example at about $-50$ to about $-10°$ C. particularly if the reaction mixture contains highly reactive reagents. After acylation has commenced, the temperature can be raised up to about 150° C. or even higher if desired, for example, to increase the rate of reaction. It is generally preferred to carry out the reaction at temperatures in the range of between about $-30°$ C. and $+25°$ C. (room temperature).

A non-protic diluent can also be employed, if desired. Advantageously, the diluent should dissolve the Lewis acid/inorganic salt controlling agent complex and the Lewis acid/acyl compound complex. It should also be relatively inert toward Friedel-Crafts reactions. Preferred diluents include, for example, methylene chloride, carbon disulfide, odichlorobenzene, 1,2,4-trichlorobenzene, o-difluorobenzene, 1,2-dichloroethane, 1,1,2-trichloroethene, 1,1,2,2-tetrachloroethane, tetrachloroethene and mixtures thereof. In certain cases it may be advantageous to use an excess of the aromatic reactant, which also serves as a solvent for the reaction.

If a diluent such as methylene chloride or dichloroethane is used, although we do not wish to be bound to any particular explanation it is believed that the Lewis acid/inorganic salt controlling agent complex reduces the tendency of the diluent act as an alkylating agent by competing with the diluent for available Lewis acid and thereby suppressing alkylation of reactant and/or product. Alkylation of the aromatic component in the para or ortho position introduces undesirable impurities which often are difficult to remove by conventional purification methods.

The diluent is preferably used in an amount from 20 to about 93% by weight, based on the weight of the total reaction mixture. It has been found that the reagent to diluent molar ratio can contribute to control of the reaction to yield the desired product. Typically the diluent is used in an amount of at least about 20%, preferably at least about 30% by weight based on the weight of the reaction mixture. Typically the diluent is also used in an amount of less than 93%, preferably less than 80%, most preferably less than 60%.

Use of an alkylating or acylating diluent can lead to undesired side reactions as mentioned above. When such solvents are employed, control of the reaction by techniques taught in this specification suppresses such alkylation or arylation. The result is an aryl carbonyl or sulfonyl compound of outstanding purity and/or degree of para substitution.

The compound produced contains catalyst residues complexed to the carbonyl group. Decomplexation can be accomplished by treating the reaction mixture with a decomplexing base after completion of the reaction. The base can be added to the reaction medium or the reaction medium can be added to the base. The decomplexing base must be at least as basic towards the Lewis acid as the basic groups on the polymer chain. Such decomplexation preferably should be effected before isolation of the product from the reaction mixture.

The following examples illustrate the process of this invention using a variety of Lewis acids, inorganic salt controlling agents, diluents and reagents. It is to be understood that other reactants and reaction media within the scope of the teaching of this invention can be employed, if desired.

EXAMPLE 1

To an agitated mixture of lithium chloride (3.18 g., 0.075 mole) and aluminium chloride (20 g., 0.15 mole) in dichloroethane (20 ml) at −15° C. was added dropwise a mixture of 4-fluorobenzoyl chloride (8 g., 0.05 mole) and fluorobenzene (4.8 g., 0.05 mole) in dichloroethane (7 ml). The reaction mixture was removed from the water bath after one hour, stored at 0° C. for three hours then at room temperature overnight.

The reaction mixture was then slowly added to 100 mls of a stirred mixture of ice and dilute aqueous hydrochloric acid, the organic phase separated and the aqueous phase was washed with two 50 ml aliquots of ether. The combined organic phases were then washed with 50 ml of dilute sodium hydroxide solution, then water, separated and dried over anhydrous magnesium sulfate. The dried solution was filtered to remove the drying agent and the solvents removed in a rotary evaporator. 4,4'-Difluorobenzophenone (10.3 g., 94.5% yield) was obtained as a white solid of melting point 106.5°–109° C., whose purity was estimated by differential scanning calorimetry (DSC) by the reference test method described in U.S. Pharmacopaeia National Formulary, XIX,— pages 980 to 983 (1975) and also by R.L. Blaine in the DuPont Company, Analytical Instruments Division Application Brief Number TA.80, and also by 1H and 19F nuclear magnetic resonance (NMR). The purity by the DSC method was estimated to be 97.2% and by the 1H NMR method about 95%.

EXAMPLE 2

In an experiment not using the process of the instant invention but following the teachings of traditional Friedel-Crafts chemistry, that is in the absence of lithium chloride and in the presence of aluminum chloride in an amount of 8 g., (0.06 mole), which is less than 1.5 equivalents per equivalent of 4-fluorobenzoyl chloride, the remaining ingredients being as described in example 1, the addition was commenced at 0° C. and the reaction mixture maintained at room temperature overnight. After work up as described in example 1, an orange oil was obtained in low yield. 1H NMR indicated only 50% of the product was the desired 4,4'-difluorobenzophenone, the remainder being isomers, impurities and starting materials. When this experiment was repeated using 20 g., (0.15 mole) of aluminium chloride the yield of crude reaction product increased to 93%, about half of which was the desired 4,4'-difluorobenzophenone.

EXAMPLE 3

Example 1 was repeated except that 20 g., (0.208 mole) fluorobenzene was used and the reaction mixture was kept at 0° C.-overnight. The crude yield of 4,4'-difluorobenzophenone was 92.3% (m.p. 108–110° C.; DSC purity 97.4 mol %, 1H NMR purity >95 mol %). 19F NMR indicated about 0.1% ortho acylation. After recrystallization from hexane the yield was 64%, the DSC purity was 99.75% and 19F NMR showed no evidence of ortho substituted (i.e., isomeric) impurities.

EXAMPLE 4

The procedure and materials of Example 3 were used except that 5.75 g., (0.025 mole) terephthaloyl chloride was used in place of 4-fluorobenzoyl chloride and the reaction mixture was kept at about −5° C. for three days. The crude product 1,4-bis(4-fluorobenzoyl) benzene (6.98 g., 86.7% yield, m.p. 220.5-222° C.) had a purity by 1H NMR greater than 95% and 19F NMR indicated no ortho isomers to be present.

EXAMPLE 5

To an agitated mixture of lithium chloride (3.18 g., 0.075 mole) and aluminium chloride (20 g., 0.15 mole) in dichloroethane (20 ml) at about −15° C. was added 4-fluorobenzoyl chloride (9.6 g., 0.06 mole) and diphenyl ether (4.25 g., 0.025 mole) in dichloroethane (10 ml). The reaction mixture was maintained at −15° to −17° C. for one hour then 0° C. for three hours then left at about −5° C. for three days. After working up as described in Example 1 the 4,4'-bis(4-fluorobenzoyl)-diphenyl ether obtained (9.34 g., 90% yield, m.p. 214.5°–215.5° C.) had a 1H NMR purity of over 99% and the DSC purity was 99.5%.

EXAMPLE 6

The materials and procedures of Example 5 were repeated except that the lithium chloride was omitted and the reaction was held at about −5° C. for three days, after one hour at −15° C. The 4,4'-bis(4fluorobenzoyl)diphenyl ether obtained (10.36 g., 100% yield, m.p. 213°–215° C.) had a 1H NMR purity of >95% and a DSC purity of 97.6%. 19F NMR indicated an absence of ortho-substituted isomers.

EXAMPLE 7

In an experiment not following the teachings of the instant invention Example 9 was repeated except that no lithium chloride was used, only 9.6 g., (0.072 mole) aluminium chloride was present and the reaction mixture was kept at 0° C. overnight then worked up. 3.92 g., (38% yield) of crude 4,4'-big(fluorobenzoyl)diphenyl ether of 1H NMR purity 80% was obtained.

EXAMPLE 8

To an agitated mixture of aluminium chloride (20 g., 0.15 mole) and lithium chloride (3.18 g., 0.075 mole) and dichloroethane (20 ml) at −15° C. was slowly added toluene (4.6 g., 0.05 mole) and acetyl chloride (3.93 g., 0.05 mole) in dichloroethane (10 ml). The reaction mixture was left at −15° C. for one hour then allowed to warm up to room temperature overnight. After working up as described in Example 1, the 4-methylacetophenone obtained (7.17 g.), had a 1H NMR estimated purity of about 95%. 1H NMR showed less than 2% ortho isomers.

EXAMPLE 9

The materials and procedures of Example 8 were followed except that benzoyl chloride (7.0 g., 0.05 mole) was used instead of acetyl chloride. The 4-methylbenzophenone obtained (8.62 g., 88% yield) had a 1H NMR purity of 95% and a DSC purity of 97.7%. Gas chromatography (G.C.) indicated the presence of less than 2% ortho isomers.

EXAMPLE 10

To an agitated mixture of lithium chloride (3.18 g., 0.075 mole) and aluminium chloride (20 g., 0.15 mol) in dichloroethane (20 ml) was slowly added diphenyl ether (8.51 g., 0.05 mole) and acetyl chloride (3.93 g., 0.05 mol) in dichloroethane (7 ml) following the procedure of example 9. The 4-phenoxyacetophenone obtained (9.57 g., 90.3% yield, m.p. 43.5°–51° C.) had a 1H NMR purity of 90%.

EXAMPLE 11

The materials and procedures of Example 10 were used except that acetic anhydride (5.1 g., 0.05 mole) was used instead of acetyl chloride. The 4-phenoxyacetophenone obtained (9.75 g., 92% yield, m.p. 46°–51.5° C.) had a 1H NMR purity of 90%, the major impurity being unreacted diphenyl ether.

EXAMPLE 12

The materials and procedures of Example 10 was used except that benzoyl chloride (7.03 g., 0.05 mole) was used instead of acetyl chloride. The p-phenoxybenzophenone obtained (12.83 g., 93.6% yield) had a 1H NMR purity of 90%, unreacted diphenyl ether being the main impurity.

EXAMPLE 13

The materials and procedures of Example 10 were used except that only 4.20 g., (0.025 mole) of diphenyl ether were used and 4-chlorobenzoyl chloride (10.5 g., 0.06 mole) was used instead of acetyl chloride. The reaction product was poured into dilute hydrochloric acid-ice mixture, separated, suspended in methanol, filtered and dried in vacuum at 80° C. (This procedure was used because this product is insoluble in common solvents.) The 4,4'-bis(4-chlorobenzoyl)diphenyl ether obtained (10.84 g., 97% yield, m.p.244-248° C) had a DSC purity of 98.1%.

EXAMPLE 14

To an agitated mixture of lithium Chloride (3.18 g., 0.075 mole) and aluminium chloride (20 g., 0.15 mole) in dichloroethane cooled to below −10° C. was added anisole (5.41 g.,−0.05 mole) and benzoyl chloride (7.03 g., 0.05 mole) in dichloroethane (10ml). The reaction mixture was held below −10° C. for one hour then allowed to come to room temperature overnight. The 4-methoxybenzophenone produced (9.55 g., 90.1% yield) had a gas chromatograph/mass spectrometer estimated purity of over 95% with 2% ortho isomers.

EXAMPLE 15

To a solution of diphenyl ether (3.57 g., 0.021 mole) in dichloroethane (15 ml) at −15° C. was added, by means of a bubbler, phosgene (0.87 g., 0.01 mole). The combined reactants were then added to an agitated mixture of lithium chloride (0.64 g., 0.015 mole) and aluminum trichloride (3.67 g., 0.0275 mole) in dichloroethane (20 ml) at −15° C. The reaction mixture was allowed to warm up to room temperature over 1.25 hours. After 68 hours at room temperature, the reaction mixture was worked up as described in example 1 to yield crude 4,4'-diphenoxy-benzophenone (2.2 g, 60% yield) of DSC purity 96.6%.

EXAMPLE 16

The procedure and materials of example 5 were used except that the same volumes of carbon disulfide are used as diluent instead of dichloroethane. The crude 4,4'-bis(4fluorobenzoyl)diphenyl ether obtained (9.25 g., 89.4% yield) had a DSC purity of 95%. IH and 19F NMR both indicated 95% purity.

EXAMPLE 7

The materials and procedures of example 9 were used except that the lithium chloride was omitted. The crude 4-methylbenzophenone obtained (8.15 g., 83.2% yield) had a purity as estimated by G.C. and 1H NMR of 90%.

EXAMPLE 18

In an experiment not following the teachings of the instant invention, Example 8 was repeated except that no lithium chloride was used and only 8.0 g (0.06 mole) aluminum chloride was present. After working up in the same way as example 8, 4-methylacetophenone was obtained with a 1H NMR purity of 80 to 85%. GC/MS indicated an impurity with a mass of 324 Daltons was present.

EXAMPLE 19

In an experiment not following the teachings of the instant invention, Example 11 was repeated except that no lithium chloride was used and only 8.0 g (0.06 mole) aluminum chloride was present. The 4-phenoxyacetophenone obtained had an 1H NMR purity of 80 to 85%, the main impurities being about 5% unreacted diphenyl ether and about 10% of the diacetylated product.

EXAMPLE 20

In an experiment not following the teachings of the instant invention, Example 13 was repeated except that no lithium chloride and only 9.6 g (0.072 mole) aluminum chloride was present. The 4,4'-bis(4-chlorobenzoyl)diphenyl ether was obtained in 86 yield.

What is claimed is:

1. A process for the preparation of an aromatic carbonyl compound having the formula

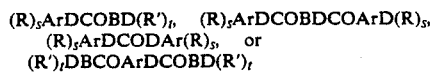

wherein each s and t is independently 1, 2 or 3 and each R, Ar, B, D and R' is independently as defined below, which comprises reacting a first reactant, consisting of a substituted or unsubstituted aromatic compound containing at least one activated hydrogen atom of the formula (R)₅ArDH wherein Ar is a homo or hetero-aromatic mono-, di- or tricyclic moiety or a fused homo-aromatic condensed system containing less than 20 aromatic carbon atoms, or a heteroaromatic system containing less than 8 nitrogen atoms, each R is as defined below and D is —(ZAR)ₙ—(ZAr)ₘ—(ZAr)ₚ— wherein n, m, and p are each independently 0, 1, 2 or 3, provided that n+m+p is less than 4, and Z is —CO—, —SO₂—, [—CO—C₆H₄H4—CO—
—CO—C₆H₄CO—, or —O(CF₂)_qO— or V, provided that when n+m+p>0, any Ar group which contains an activated hydrogen atom is also linked to a V group, where V is a divalent radical of the formula —O—, —S—, —N=N—, —(CF₂)_q—, —(CH₂)_q—,
or —C(CH₃)₂— wherein q is 1 to 20;
with a second reactant, consisting of phosgene, or a monofunctional acyl compound of the general formula YCOBD(R')_t or O(COBD(R')_t)₂ or a di-functional acy compound of the general formula

YCOBDCOY wherein each B is independently a divalent substituted or unsubstituted aliphatic or cycloaliphatic group or Ar, and R and R' which may be the same or different are a H, Br, Cl or F atom or a hydroxy, alkoxy, alkyl, aralkyl, unsubstituted or mono- or disubstituted amino, nitro, ester, acid, amide or imide group, and each Y represents a Br, Cl or F atom or a hydroxy or alkoxy group, subject to the proviso that any aromatic ring which contains an activated hydrogen atom also contains no alkoxy groups and to the further proviso that the aromatic carbonyl compound contains less than 2 identical directly linked sequences containing at least one —SO₂— or —CO—
. in a reaction medium comprising:
(A) an inorganic salt controlling agent in an amount from 0.1 to 4 equivalents per equivalent of acid, ester or acid halide group in the reactants;
(B) a Lewis acid selected from the group consisting of aluminum trichloride, aluminum tribromide, antimony pentachloride, antimony pentafluoride, indium trichloride, gallium trichloride, boron trichloride, boron trifluoride, ferric chloride, stannic chloride, titanium tetrachloride, and molybdenum pentachloride, in an amount of about one equivalent per equivalent of carbonyl, or other basic species in the reactants plus one equivalent per equivalent of Lewis base plus an amount effective to act as a catalyst for the reaction; and
(C) a non-protic diluent in an amount from about 20 to about 93% by weight, based on the weight of the total reaction mixture.

2. A process according to claim 1, wherein the inorganic salt controlling agent is a chloride, perchlorate, or trifluoromethanesulfonate salt.

3. A process according to claim 2, wherein the inorganic salt controlling agent is trimethylammonium chloride, tetramethylammonium chloride, sodium chloride, or lithium chloride.

4. A process according to claim 1, wherein the aromatic carbonyl compound produced has the structure (R')_t DBCOArDCOBD(R')_t and the first reactant contains 2 activated hydrogen atoms.

5. A process according to claim 1, wherein the aromatic compound is selected from benzene, toluene, ethylbenzene, fluorobenzene, chlorobenzene, bromobenzene, anisole, ethoxybenzene, 3-chloroanisole, naphthalene, anthracene, and

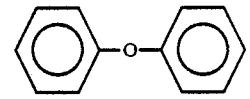

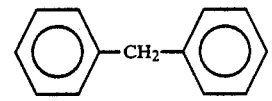

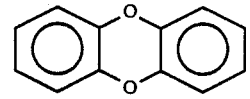

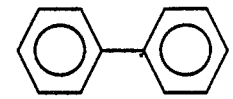

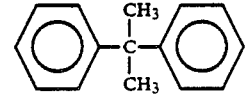

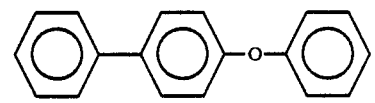

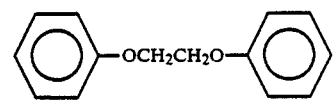

wherein each a is independently 0, 1, or 2.

6. A process according to claim 1, wherein the organic mono— or diacid compound is selected from the group consisting of acetic anhydride, acetyl chloride, oxalyl dichloride, adipoyl chloride, benzoyl chloride, 4-fluorobenzoyl chloride, 4-chlorobenzoyl chloride, 3-nitrobenzoyl chloride, terephthaloyl chloride, isophthaloyl chloride, phthaloyl chloride, phthalic anhydride, naphthoyl chloride, tetrabromophthaloyl chloride, and compounds of the following formulas where a is 0, 1, or 2.

7. A process according to claim 1, wherein the diluent is selected from methylene dichloride, carbon disulfide, o-dichlorobenzene, 1,2,4-trichlorobenzene, o-difluorobenzene, 1,2-dichloroethane, tetrachloroethane, 1,1,2,2-tetrachloroethane, and mixtures thereof.

* * * * *